United States Patent

Rosch et al.

[11] Patent Number: 5,876,394
[45] Date of Patent: Mar. 2, 1999

[54] INTEGRAL DISPOSABLE WASTE CONTAINMENT ARTICLE

[75] Inventors: Paulette Mary Rosch, Sherwood; Ingrid Christine Hollrah, Neenah, both of Wis.

[73] Assignee: Kimberly-Clark Worldwide, Inc., Neenah, Wis.

[21] Appl. No.: 748,049

[22] Filed: Nov. 12, 1996

Related U.S. Application Data

[63] Continuation of Ser. No. 283,100, Jul. 29, 1994, abandoned.

[51] Int. Cl.⁶ .................................................. A61F 13/15
[52] U.S. Cl. ......................... 604/393; 604/367; 604/371; 604/378; 604/385.1; 604/385.2
[58] Field of Search .................................. 604/364, 385.1, 604/385.2, 373, 393–402, 370, 372, 386, 374, 367, 371, 378

[56] References Cited

U.S. PATENT DOCUMENTS

| | | | |
|---|---|---|---|
| 876,173 | 1/1908 | Guttman . | |
| 2,629,380 | 2/1953 | Schweikert | 128/284 |
| 2,678,648 | 5/1954 | De Woskin | 128/288 |
| 2,842,129 | 7/1958 | Ernstorff | 128/288 |
| 3,025,856 | 3/1962 | Burwell et al. | 128/288 |
| 3,043,307 | 7/1962 | Weston | 128/295 |
| 3,237,625 | 3/1966 | Johnson | 128/288 |
| 3,368,563 | 2/1968 | Scheier | 128/288 |
| 3,599,640 | 8/1971 | Larson | 128/286 |
| 3,613,687 | 10/1971 | Kennedy | 128/288 |
| 3,636,953 | 1/1972 | Benevento | 128/291 |
| 3,648,699 | 3/1972 | Anderson et al. | 128/288 |
| 3,714,946 | 2/1973 | Rudes | 128/295 |
| 3,720,212 | 3/1973 | Kaupin | 128/288 |
| 4,100,324 | 7/1978 | Anderson et al. | 428/288 |
| 4,114,621 | 9/1978 | Mims, Jr. | 128/288 |
| 4,145,763 | 3/1979 | Abrams et al. | 2/403 |
| 4,227,531 | 10/1980 | McLeod | 128/288 |
| 4,324,245 | 4/1982 | Mesek et al. | 128/287 |
| 4,337,771 | 7/1982 | Pieniak et al. | 128/287 |
| 4,340,563 | 7/1982 | Appel et al. | 264/518 |
| 4,388,075 | 6/1983 | Mesek et al. | 604/385 |
| 4,405,297 | 9/1983 | Appel et al. | 425/72 S |
| 4,555,245 | 11/1985 | Armbruster | 604/396 |
| 4,578,073 | 3/1986 | Dysart et al. | 604/385.2 |
| 4,606,964 | 8/1986 | Wideman | 428/152 |
| 4,639,949 | 2/1987 | Ales et al. | 2/402 |
| 4,657,802 | 4/1987 | Morman | 428/152 |
| 4,690,680 | 9/1987 | Higgins | 604/386 |
| 4,699,620 | 10/1987 | Bernardin | 604/385 |
| 4,704,116 | 11/1987 | Enloe | 604/385 A |
| 4,720,415 | 1/1988 | Vander Wielen et al. | 428/152 |
| 4,747,846 | 5/1988 | Boland et al. | 604/38 A |
| 4,773,903 | 9/1988 | Weisman et al. | 604/370 |
| 4,798,603 | 1/1989 | Meyer et al. | 604/378 |
| 4,865,596 | 9/1989 | Weisman et al. | 604/370 |
| 4,938,753 | 7/1990 | Van Gompel et al. | 604/385.2 |
| 4,938,754 | 7/1990 | Mesek | 604/385.2 |

(List continued on next page.)

FOREIGN PATENT DOCUMENTS

| | | |
|---|---|---|
| 1299321 | 4/1992 | Canada . |
| 0283930 | 9/1988 | European Pat. Off. . |
| 0539703 | 5/1993 | European Pat. Off. . |
| 0539703A1 | 5/1993 | European Pat. Off. ........ A61F 13/15 |
| 0547497 | 6/1993 | European Pat. Off. . |
| 2244422 | 12/1981 | United Kingdom . |
| 2244422 | 12/1991 | United Kingdom .................. 604/396 |
| 2269978 | 3/1994 | United Kingdom . |
| 2269998 | 3/1994 | United Kingdom . |
| 2269999 | 3/1994 | United Kingdom . |
| WO 95/18589 | 7/1995 | WIPO . |

*Primary Examiner*—Mickey Yu
*Assistant Examiner*—Francis K. Cuddihy
*Attorney, Agent, or Firm*—Brinks Hofer Gilson & Lione

[57] ABSTRACT

A disposable waste containment article includes a waste containment structure that has an absorbent core which is positioned between a wearer and a backsheet and held in place by a primary elastic, and a cover joined to the waste containment structure. Methods are provided for making the waste containment article.

10 Claims, 4 Drawing Sheets

U.S. PATENT DOCUMENTS

| | | | |
|---|---|---|---|
| 4,938,757 | 7/1990 | Van Gompel et al. | 604/396 |
| 4,940,464 | 7/1990 | Van Gompel et al. | 604/396 |
| 5,087,253 | 2/1992 | Cooper | 604/385.1 |
| 5,114,781 | 5/1992 | Morman | 428/198 |
| 5,116,662 | 5/1992 | Morman | 428/198 |
| 5,188,627 | 2/1993 | Igaue et al. | 604/385.2 |
| 5,246,433 | 9/1993 | Hasse et al. | 604/385.1 |
| 5,263,948 | 11/1993 | Karami et al. | 604/385.1 |
| 5,300,054 | 4/1994 | Feist et al. | 604/385.1 |
| 5,304,161 | 4/1994 | Noel et al. | 604/385.1 |
| 5,370,634 | 12/1994 | Ando et al. | 604/385.1 |
| 5,439,458 | 8/1995 | Noel et al. | 604/385.1 |
| 5,549,775 | 8/1996 | Odorzynski | 604/385.1 |
| 5,599,335 | 2/1997 | Goldman et al. | 604/372 | ns

INTEGRAL DISPOSABLE WASTE CONTAINMENT ARTICLE

This is a continuation of U.S. application Ser. No. 08/283,100 filed Jul. 29, 1994, now abandoned.

BACKGROUND OF THE INVENTION

This invention pertains to disposable waste containment articles, and more particularly to articles providing containment and absorbency of waste matter while being useful as a swimsuit garment.

Currently, disposable waste containment articles find widespread use in the areas of adult care, infant care, and child care, and have generally replaced reusable cloth articles. Disposable diapers, for example, have met a particular need and have become very popular. Disposable training pants have also met a particular need and have become popular. A problem exists with the design of children's swimsuits. Boys' boxer-style suits contain a liner, and girls' suits are made of stretchy, body-hugging materials. Neither swimsuit is designed to accommodate a dry diaper well, and especially when the diaper/pant is wet and swollen. Further, the design does not keep the current suits with diaper or pants in place during swimming and after swimming.

SUMMARY OF THE INVENTION

Thus, there is a need to provide an improved child's swimming apparel that minimizes the leakage of urine and fecal matter during travel to swimming while maintaining fecal containment during swimming. In response to this need, a new waste containment garment and method of making a waste containment garment have been discovered. A waste containment garment according to the invention includes a waste containment structure having a longitudinal axis and opposite longitudinally spaced ends and a cover defining opposite waist regions. The waste containment structure comprises an absorbent core, a backsheet and an elastic element located outside of the waist regions to hold the structure in place. The elastic is not operatively joined to the cover. The waste containment structure can remain snugly in place while resisting movement in response to the cover.

In another aspect of the invention, a three-dimensional waste containment garment includes a waist containment structure and a cover. The full cover has an outer surface and possibly an opposing inner surface and defines at least a waist opening. The cover is joined to the waste containment structure at least at a portion of the waist opening. A waste containment structure of the garment has a longitudinal axis, opposite longitudinally spaced ends, and side edges extending between the ends. The waste containment structure includes a liquid permeable liner, a backsheet attached to the liner, and an absorbent core sandwiched between the liner and backsheet. The cover is elastically connected to the ends of the waste containment structure.

Another aspect of the invention relates to a method of making a three-dimensional waste containment garment. The method includes: supplying a cover; supplying a waste containment structure having opposite longitudinally spaced ends, the waste containment structure comprising an absorbent core and a backsheet, elasticizing at least a portion of the waste containment structure; connecting a waist region of the cover to the waste containment structure, and bonding portions of the side panels of the structure together to define a waist opening and a pair of leg openings.

Numerous features and advantages of the present invention will appear from the following description. In the description, reference is made to the accompanying drawings which illustrate preferred embodiments of the invention. Such embodiments do not represent the full scope of the invention. Reference should, therefore, be made to the claims herein for interpreting the full scope of the invention.

BRIEF DESCRIPTION OF THE DRAWINGS

The above-mentioned and other features of the present invention and the manner of attaining them will become more apparent, and the invention itself will be better understood by reference to the following description of the invention, taken in conjunction with the accompanying drawings, wherein.

DEFINITIONS

Figure 1:
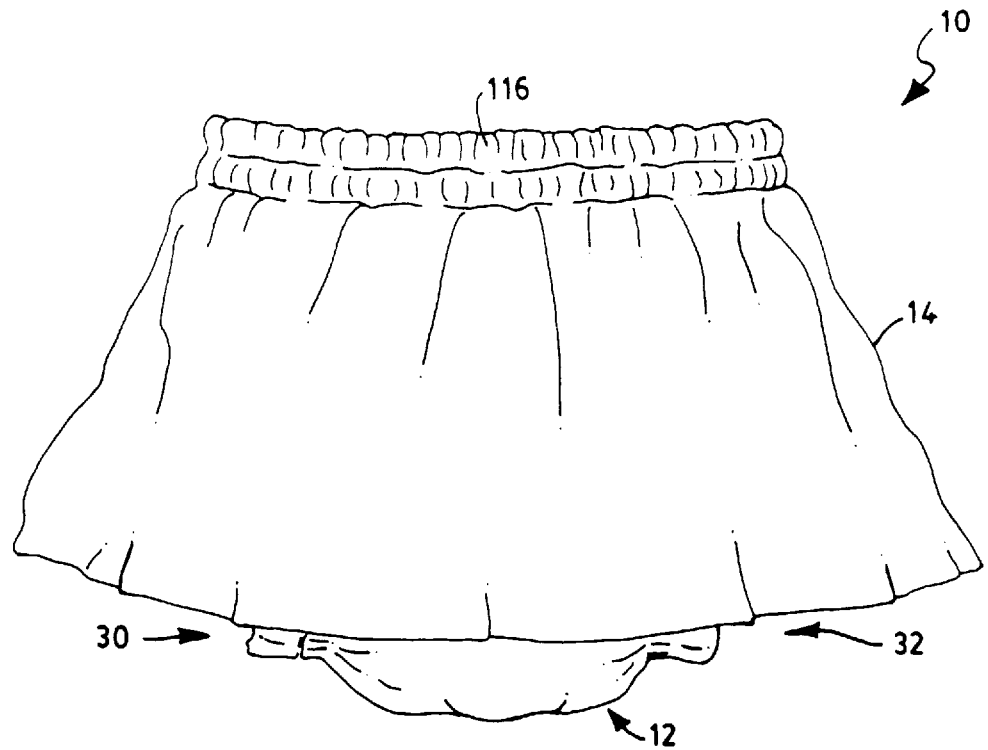
FIG. 1 is a front view of a pant typifying an embodiment of the present invention for a girl's swimsuit.

Within the context of this specification, each term or phrase below will include the following meaning or meanings:

(a) "Bonded" refers to the joining, adhering, connecting, attaching, or the like, of two elements. Two elements will be considered to be bonded together when they are bonded directly to one another or indirectly to one another, such as when each is directly bonded to intermediate elements.

(b) "Disposable" includes being disposed of after use, and not intended to be washed and reused.

(c) "Disposed", "disposed on", "disposed with", "disposed at", "disposed near", and variations thereof are intended to mean that one element can be integral or unitary with another element, or that one element can be a separate structure joined to or connected to or placed with or placed near another element.

(d) "Elasticity" and "elastic" include that property of a material by virtue of which it tends to substantially recover to its original size and shape after removal of a force causing deformation of the material.

(e) "Elastically connected" and "elastically connecting" refer to two elements being separated by and bonded to an elastic member, where the relative position of the two elements may change due to extension of the elastic member.

(f) "Elongation" includes the ratio of the extension of a material to the length of a material prior to the extension. Elongation is expressed in percent.

(g) "Extension", "extend", and "extended" include the change in length of a material due to stretching. Extension is expressed in units of length.

(h) "Force" includes a physical influence exerted by one body on another which produces acceleration of bodies that are free to move and deformation of bodies that are not free to move. Force is expressed in grams-force.

(i) "Foreshortened" and "foreshortening" include to shorten beforehand, that is, before a subsequent step.

(j) "Front" and "back" are used to designate relationships relative to the garment itself, rather than to suggest any position the garment assumes when it is positioned on a wearer.

(k) "Member" when used in the singular can have the dual meaning of a single element or a plurality of elements.

(l) "Operatively joined" with reference to the attachment of an elastic member to another element means that the elastic member when attached to or connected to or treated with heat with the element gives that element elastic properties. With reference to the attachment of a non-elastic member to another element, it means that the member and element can be attached in any suitable manner that permits or allows them to perform the intended or described function of the joinder. The joining, attaching, connecting or the like can be either directly, such as joining either member directly to an element, or can be indirectly by means of another member or element disposed between the first member and the first element.

(m) "Pervious" means that a layer of material is able to pass or transport a detectable amount of liquid under conditions normally encountered in a diaper/pant during use.

(n) "Porous" means that a layer of material is able to pass or transport a measurable amount of liquid under conditions normally encountered in a diaper/pant during use.

(o) "Rupture" includes the breaking or tearing apart of a material; in tensile testing, rupture refers to the total separation of a material into two parts either all at once or in stages, or the development of a hole in some materials.

(p) "Stretch bonded" refers to an elastomeric strand being bonded to another member while the elastomeric strand is elongated at least about 25 percent of its relaxed length. Desirably, the term "stretch bonded" refers to the situation wherein the elastomeric strand is elongated at least about 100 percent, more desirably at least about 300 percent, of its relaxed length when it is bonded to the other member.

(q) "Stretch bonded laminate" ("SBL") refers to a composite material having at least two layers in which one layer is a gatherable layer and the other layer is a stretchable, that is, elastic, layer. The layers are joined together when the stretchable layer is in a stretched condition so that upon relaxing the layers, the gatherable layer is gathered.

(r) "Tension" includes a uniaxial force tending to cause the extension of a body or the balancing force within that body resisting the extension.

(s) "Two-dimensional" refers to a garment, such as a diaper, that can be opened and laid in a flat condition without destructively tearing any structure. This type of garment does not have continuous leg and waist openings when opened and laid flat, and requires a fastening device, such as adhesive tapes, to attach the garment about the wearer.

(t) "Three-dimensional" refers to a finished garment similar to shorts or pants in that they have continuous leg and waist openings that are bounded by the material of which the garment is made. This type of garment can be opened and laid flat only by destructively tearing it. This type of garment may or may not have manually tearable seams.

(u) "Ultimate elongation" includes the elongation at the point of rupture.

These definitions are not intended to be limiting and these terms may be defined with additional language in the remaining portion of the specification.

DESCRIPTION OF A PREFERRED EMBODIMENT

Figure 2:
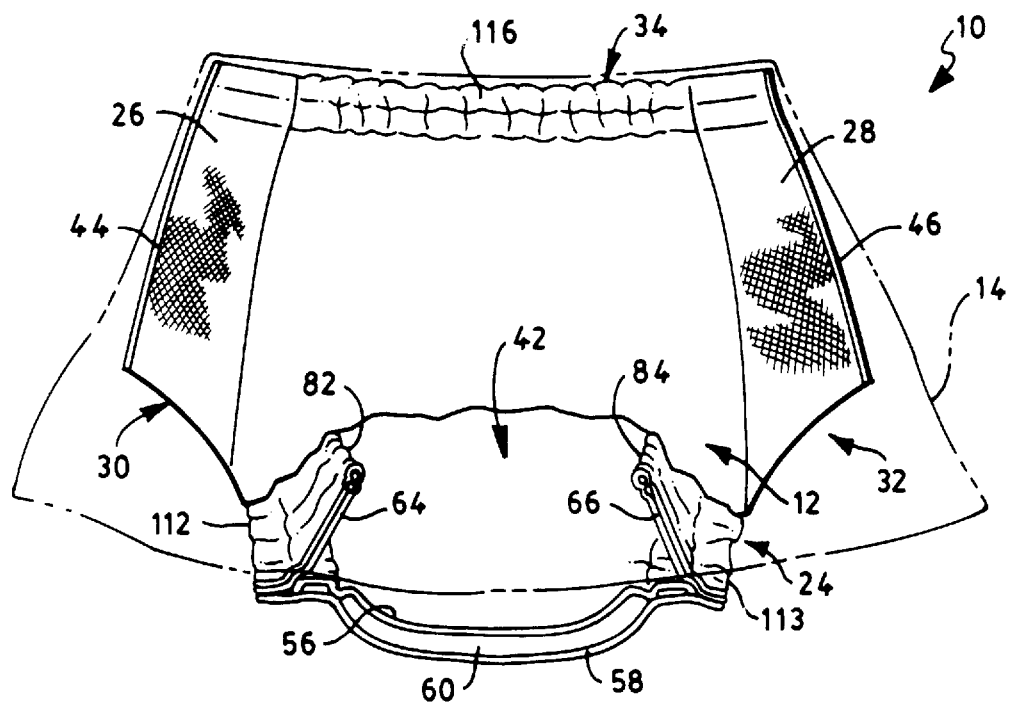
FIG. 2 is a front view of a pant typifying an embodiment of the present invention for a girl's swimsuit.

A pant 10 using this invention, shown in FIGS. 1 and 2, includes a waste containment structure 12 and a suspended cover 14. Pant 10 is intended to resemble swimwear or outer active water immersible clothing. At the same time, the pant 10 is constructed such that the cover 14 remains securely in place about the child's waist with the waste containment structure 12 positioned to receive and contain voided material. Pant 10 can be made or constructed in a variety of ways, one of which is described in U.S. Pat. application Ser. No. 043,132 filed on Mar. 25, 1993, which is incorporated by reference herein. Other pant designs are described in U.S. Pat. Nos. 4,938,757, 4,747,846, and 4,940,464; the contents of these three patents are incorporated by reference herein.

Figure 6:
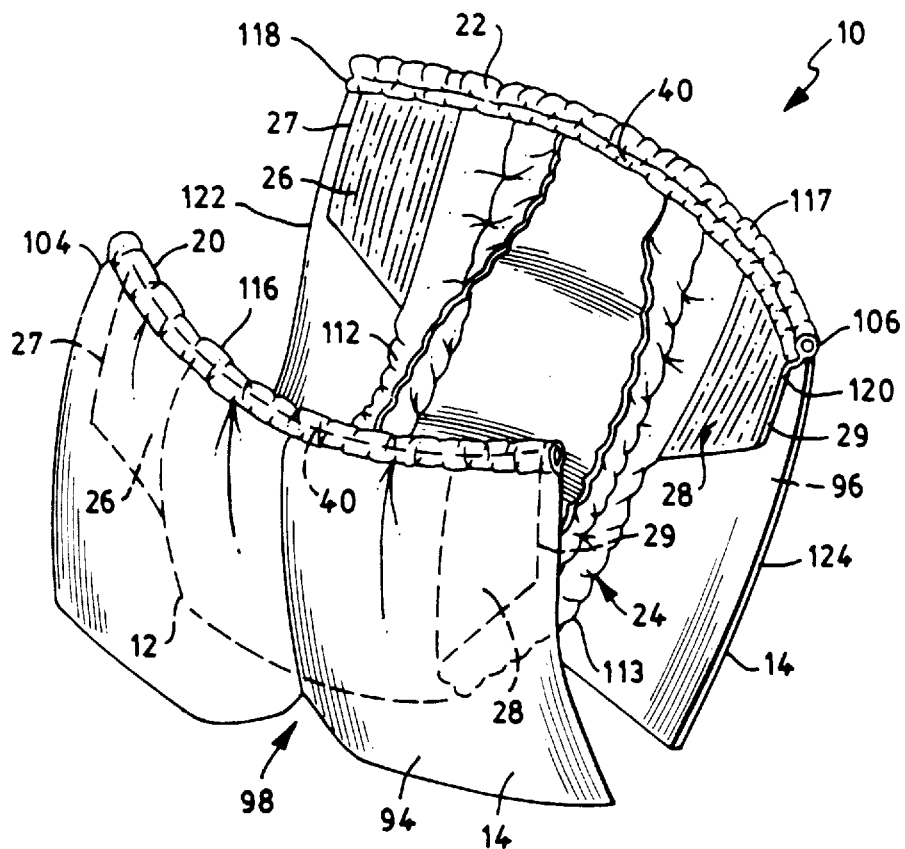
FIG. 6 is a perspective view of a pant for a boy's swimsuit showing the invention in an opened out view.

The pant 10 is illustrated partially opened out in FIG. 6. The cover 14 includes opposite inner and outer surfaces. The waste containment structure 12 also includes front and back longitudinally spaced waist regions 20 and 22, which terminate in longitudinal ends of the pant 10. A crotch area 24 is located between the front and back waist regions 20 and 22. Left and right side panels 26 and 28 extend between the front and back waist regions 20 and 22. In FIGS. 2 and 6, the waist regions 20 and 22 together with crotch area 24 form a waste containment section 42. Waste containment section 42 may include backsheet 58, liner 56, absorbent core 60 and side panels 26 and 28, and optionally containment flaps 64 and 66.

As illustrated most clearly in FIGS. 2 and 6, the edges 27 and 29 of side panels 26 and 28 may be bonded together to form manually tearable, non-refastenable seams 44 and 46. The seams 44 and 46 may be formed by any suitable means such as ultrasonic sealing, adhesive bonding, heat sealing, or the like. One suitable method of forming such seams is disclosed in U.S. Pat. No. 4,938,753 issued Jul. 3, 1990, to Van Gompel et al., which is incorporated herein by reference. The waste containment structure 12 thus defines a waist opening 34 and a pair of leg openings 30 and 32 (FIGS. 1 and 2).

Waste containment structure 12 generally comprises waste containment section 42 and side panels 26 and 28 and a primary elastic to hold the structure in place on the wearer. The structure 12 does not use waist elastics to hold the structure in place. Desirably the structure 12 is held in place without any use of waist elastics. As shown most clearly in FIG. 6, the waste containment structure 12 is elastically held in place on the wearer independent of any elastic contained in the cover 14 and, preferably, independent of any elastic in the waist region. The term "independent" in this context means that while the waste containment structure 12 is connected to the cover 14, the cover 14 can move relative to the waste containment structure 12.

Side panels 26 and 28, which may or may not have elastic characteristics, are ultrasonically bonded and are formed such that the materials of construction provide a manually tearable, non-refastenable region near the seams 44 and 46.

The side panels 26 and 28 can incorporate the primary elastic and be rendered elastic by incorporating a layer of elastic material or an SBL. The side panels 26 and 28 are either not bonded to the cover 14 or bonded in relatively limited areas. Alternatively, the structure 12 can incorporate the primary elastic and be rendered elastic by incorporating strands of elastics about the body of the structure or by incorporating a layer of elastic material or an SBL throughout the exterior of the structure 12. Although the side panels 26 and 28 can make up a portion of the longitudinal ends of the structure 12, this portion should be less than a majority of the length of the longitudinal ends and is desirably less than about 35% of the length of the longitudinal ends.

In FIG. 6 an optional secondary structure elastic in the form of a waist elastic 116 and 117 may be operatively joined to the cover 14 along the longitudinal ends 118 and 120 of waist regions 20 and 22 of the structure 12. The optional waist elastic 116 and 117 may be stretch bonded to the cover 14 or bonded in a relaxed state to a gathered portion of the cover 14. One suitable method for attaching the waist elastics 116 and 117 is disclosed in U.S. Pat. No. 4,639,949 issued Feb. 7, 1987, to Ales et al., which is incorporated herein by reference.

Alternatively, the cover 14 may be provided with an optional cover elastic, not shown, joined to the cover 14 in waist regions 104 and 106. The waist regions of the cover 14 may be attached to the waste containment structure 12 around the entirety of the waist opening or only a portion thereof. Also, both the structure 12 and cover 14 may be provided with secondary elastics in the respective waist regions, but preferably not in overlapping regions.

Alternatively, the secondary structure elastics 116 and 117 may elastically connect the front and rear waist regions 20 and 22 of the waste containment structure 12 to the waist regions 104 and 106 of the cover 14. The secondary structure elastics 116 and 117 may be bonded to the backsheet 58, the bodyside liner 56, or both using adhesives, ultrasonic bonds, thermal bonds or other suitable means.

With reference to FIGS. 2 and 6, the waste containment structure 12 as illustrated includes a backsheet 58, a substantially liquid permeable bodyside liner 56, and an absorbent core 60 sandwiched between the backsheet 58 and the liner 56. The backsheet 58 and bodyside liner 56 are desirably longer and wider than the absorbent core 60, so that the peripheries of the backsheet 58 and liner 56 form margins which may be sealed together using ultrasonic bonds, thermal bonds, adhesives, or other suitable means. The absorbent core 60 may be attached to the backsheet 58 and/or the bodyside liner 56 using ultrasonic bonds, adhesives, or other suitable means. The waste containment structure 12 may also include additional components to assist in the acquisition, distribution and storage of waste material. For example, the waste containment structure 12 may include a transport layer, such as described in U.S. Pat. No. 4,798,603 issued Jan. 17, 1989, to Meyer et al., or a surge management layer, such as described in European Patent Application EP 0 539 703 A1, published May 5, 1993, which patent and application are incorporated herein by reference.

Figure 4:
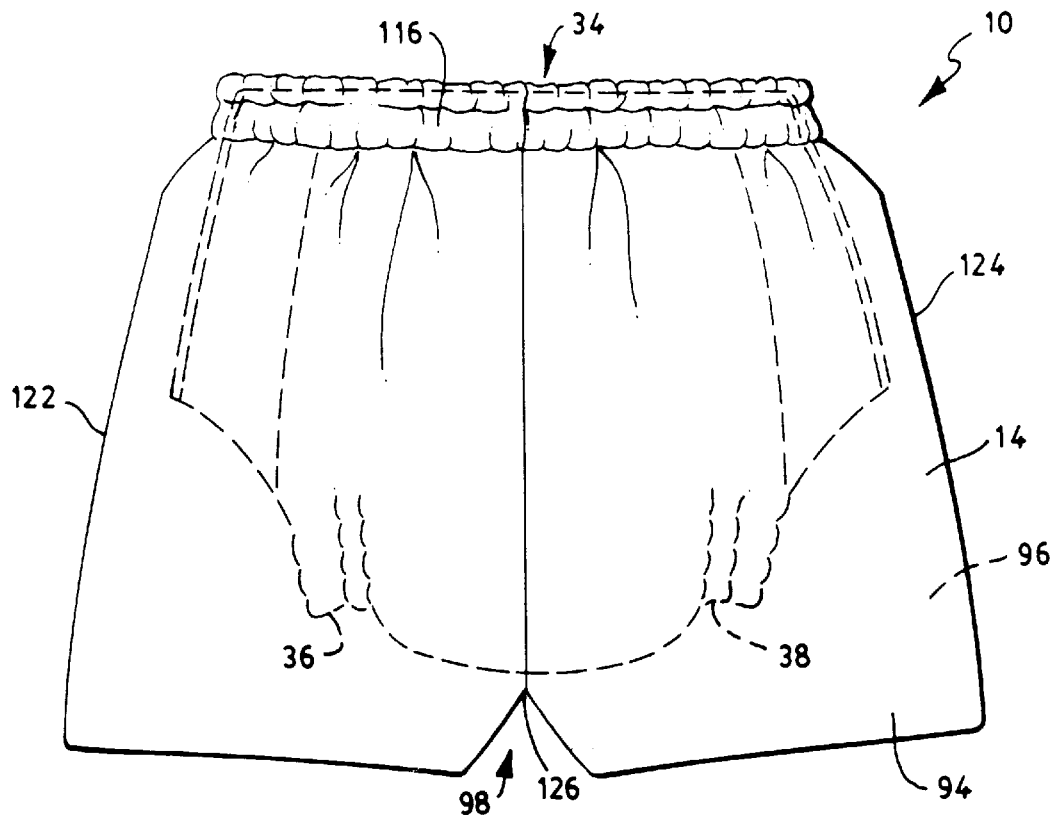
FIG. 4 is a front view of a pant for a boy's swimsuit showing the crotch area of the cover.

Referring to FIGS. 4 and 6, the cover 14 of the pant 10 preferably comprises a cover front panel 94 and a rear panel 96. The front panel 94 and the rear panel 96 of the cover 14 are joined together so as to define a crotch section 98 extending centrally between the front and rear panels 94 and 96 respectively. The front panel 94, the rear panel 96, and the crotch section 98 when joined together define a waist opening 34, and two leg openings 30 and 32 at opposite sides of the crotch section 98. The permanently attached waste containment structure 12 is preferably attached to the front panel 94 and the back panel 96, but not to the crotch section 98 of the cover 14.

The pant 10 can be formed in a continuous process by supplying a cover material including individual portions that define a single cover having waist regions 104 and 106 and front and back panels 94 and 96 extending from the waist regions. In the case of a boxer short type article, the crotch section 98 is formed between the front and back panels 94 and 96. The panels 94 and 96 can be shaped by die cutters, water jet cutters or other suitable means.

The waste containment structure 12 can be constructed by supplying bodyside liner and backsheet materials and sandwiching an individual absorbent core 60 between the backsheet 58 and bodyside liner 56. The side peripheries of the backsheet 58 and bodyside liner 56 outward of the absorbent core 60 can be joined with side panel material and sealed together. Individual waste containment structure 12 can then be cut from the continuous supply of backsheet and bodyside liner materials.

The waste containment structure 12 also desirably includes leg elastics 36 and 38 operatively joined to the backsheet 58, the bodyside liner 56, or both. The leg elastics 36 and 38 are positioned along the edges of side panels 26 and 28 and the longitudinal edges 112 and 113 of the waste containment structure 12 in the crotch area 24. The leg elastics 36 and 38 may assist in holding the waste containment structure 12 against the body of the wearer or forming seals or gaskets about the legs of the wearer.

Leg elastics 36 and 38 can be stretch bonded to the cover material along the longitudinal edges of the structure 12. The waist elastic 116 and 117 elasticize the waist regions 20 and 22 of the waste containment structure 12. Thereafter, each side panel 26 and 28 can be bonded together by seams 44 and 46 so that the waste containment structure 12 defines the waist opening 34 and the pair of leg openings 30 and 32.

In FIGS. 4 and 6, pant 10 is in a partially opened state showing edges 27 and 29 which are joined to form seams not shown, thus forming the finished pant 10. To construct the cover 14 of the preferred embodiment for pant 10, the front panel section 94 may be joined with the back panel 96 along seams 122 and 124 and in the case of a boxer short at crotch area seam 126 and to waste containment structure 12 at front and back waist regions 20 and 22 near the waist opening 34. The term "finished pant" means a three-dimensional pant that can be used for its intended purpose. The waste containment structure 12 may optionally be T-shaped, I-shaped, hourglass-shaped, or irregularly-shaped.

The swimwear-like appearance of the pant 10 is in part the result of suspending the cover 14 and optionally elasticizing the waist regions 104 and 106 of the cover. Additionally, leg elastics 36 and 38 and the primary elastic are not joined to the cover 14.

Figure 3:
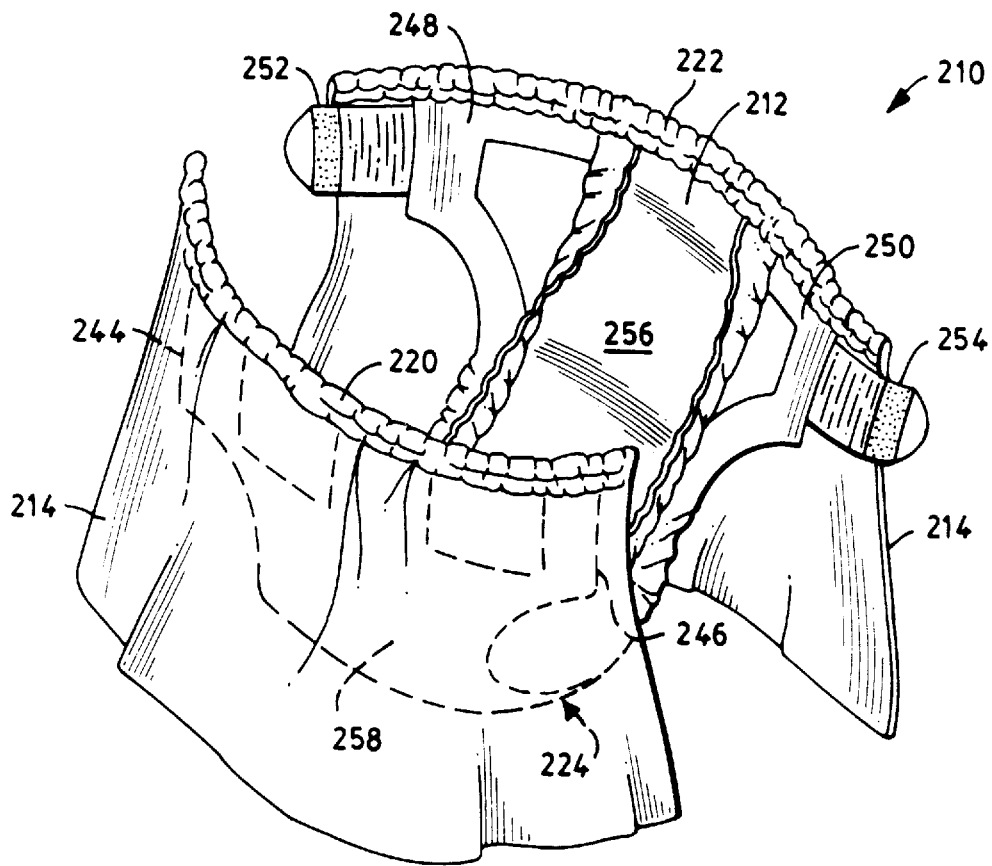
FIG. 3 is a perspective view of a diaper embodying the present invention and showing the opening/closing arrangement.
Figure 5:
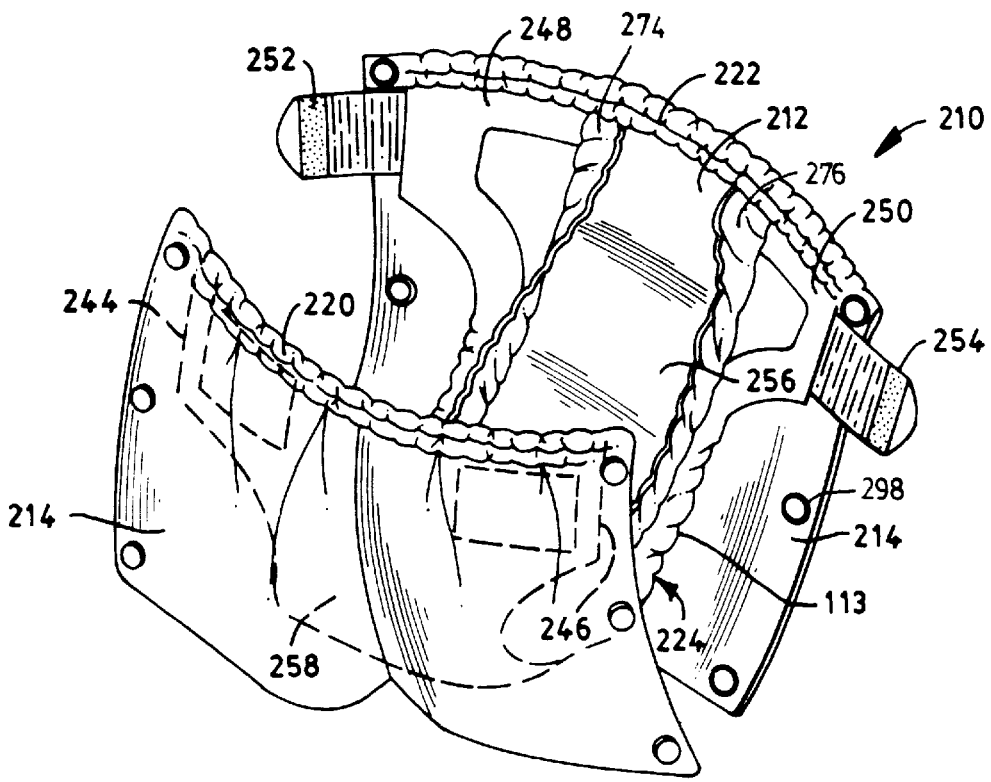
FIG. 5 is a perspective view of a diaper for a boy's swimsuit showing the present invention in particular the opening/closing arrangement for the cover.

Referring primarily to FIGS. 3 and 5, a disposable, two-dimensional garment is shown as diaper 210. The diaper 210 comprises waste containment structure 212 having front waist region 220 including oppositely disposed front ear sections 244 and 246, back waist region 222 with fasteners 252 and 254 on respective oppositely disposed back ear sections 248 and 250, and crotch area 224 between front waist region 220 and back waist region 222.

Diaper 210 further comprises a cover 214. The cover includes a front panel and back panel which at their side edges include cover fasteners 298. The cover fasteners 298 permit closure of cover 214 to form a swimsuit type garment.

The waste containment structure 212 further comprises a backsheet 258, a liner 256, and an absorbent core (not shown) disposed between backsheet 258 and liner 256. Waste containment structure 12 may include containment flaps 274 and 276.

A more detailed description of the structure of a typical diaper 210 including flaps, its process of manufacture, and method of use are contained in U.S. Pat. No. 4,704,116, which is assigned to the assignee of the present invention, the contents of which are incorporated by reference herein.

For application of the diaper to an infant and in reference to FIG. 4, the infant may be placed upon back waist region 222 of diaper 210 in preparation of fitting and attaching the diaper 210. The legs of the infant are spread apart so that front waist region 220 can be easily folded upwardly over the front of infant in a manner that snugly fits crotch area 224 against the infant. Thereafter, fasteners 252 and 254 are attached to the outermost surface of respective front ear sections 244 and 246. Then the cover fasteners 298 are closed to form a swimsuit type garment.

The absorbent core 60 can comprise a coform material composed of a mixture of cellulosic fibers and synthetic polymer fibers. For example, the coform material may comprise an airlaid blend of cellulosic wood fibers and meltblown polyolefin fibers, such as polyethylene or polypropylene fibers. Absorbent core 60 can comprise only coform, or a combination of superabsorbent materials and coform, with other absorbent or non-absorbent materials.

The coform material may comprise an airlaid blend of cellulosic wood fibers and meltblown synthetic polyolefin fibers, such as polyethylene or polypropylene fibers, or may comprise an air-formed batt of cellulosic fibers (i.e., wood pulp fluff). Optionally, the absorbent core 60 may be treated with a surfactant to aid in liquid acquisition when in a dry environment. In particular embodiments of the invention, the absorbent core 60 has a bulk thickness of not more than about 1.25 cm when dry. The hydrophilic (cellulosic) fibers and synthetic polymer fibers may be provided in a cellulosic fiber-to-synthetic polymer fiber ratio which is less than 80:20, for example between about 30:70 and about 80:20 and, desirably between about 60:40 and about 70:30.

For absorbent core 60, compounds to increase the core absorbency, are included in an effective amount and may consist of organic or inorganic high-absorbency materials. For example, the absorbent core 60 can include 0–5 weight percent high-absorbency material, preferably less than 1%. Suitable inorganic high-absorbency materials include, for example, absorbent clays and silica gels.

Organic high-absorbency materials can include natural materials, such as pectin, guar gum and peat moss, as well as synthetic materials, such as synthetic hydrogel polymers. Such hydrogel polymers may include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine or the like. Other suitable polymers can include hydrolyzed acrylonitrile grafted starch, acrylic acid grafted starch, and isobutylene maleic anhydride copolymers, and mixtures thereof.

The hydrogel polymers are preferably sufficiently cross-linked to render the materials substantially water-insoluble. Cross-linking may, for example, be by irradiation or by covalent, ionic, van der Waals or hydrogen bonding. Suitable materials are available from various commercial vendors, such as Dow Chemical Company, Hoechst-Celanese Corporation and Allied-Colloid. Typically, the high-absorbency material is capable of absorbing at least about 15 times its weight in water, and preferably is capable of absorbing more than about 25 times its weight in water.

The high-absorbency material can be distributed or otherwise incorporated into the absorbent core 60 employing various techniques. For example, the high-absorbency material can be substantially uniformly distributed among the fibers comprising the absorbent core 60. The materials can also be nonuniformly distributed within the absorbent core 60 fibers to form a generally continuous gradient with either an increasing or decreasing concentration of high-absorbency material, as determined by observing the concentration moving inward from the backsheet 58. Alternatively, the high-absorbency material can comprise a discrete layer separate from the fibrous material of the absorbent core 60, or can comprise a discrete layer integral with the absorbent core 60.

The absorbent core 60 may also include a wrap layer to help maintain the integrity of the fibrous core. This wrap may comprise a hydrophilic spunbond, meltblown or bonded-carded web material composed of synthetic polymer filaments, such as polypropylene, polyethylene, polyesters or the like or natural polymer filaments such as rayon or cotton.

The waste containment structure 12 most preferably incorporates a backsheet which is vapor pervious and liquid pervious but only to a small degree liquid pervious. It is preferably associated with a cover structure which is liquid impervious and which covers or separates the inner waste containment structure from contact with outside surfaces or people.

In the case of a boy's boxer type cover, the backsheet of the boy's waste containment structure can be made with a liquid pervious material, to allow for some breathability of the structure, while the cover is impervious, allowing for fast-drying and containment of any fluid passing through the structure.

In the case of the girl's waste containment structure, the backsheet can also be liquid-pervious, and the cover liquid-impervious, for the same reasons as above. However, when the girl's swimsuit is characterized by a skirt as a cover, the crotch area of the waste containment structure could be rendered liquid-impervious by appropriate means such as a plastic film, while the upper portion and waist of the waste containment structure 12 could be covered by a liquid-pervious material, to aid in breathability.

The backsheet 58 may comprise a thin, liquid impermeable web or sheet of plastic film such as polyethylene, polypropylene, polyvinyl chloride or similar material. Alternately, the backsheet 58 may comprise a nonwoven, fibrous web which has been suitably constructed and arranged to have low liquid perviousness. Still alternately, the backsheet 58 may comprise a layered or laminated material, such as a thermally bonded plastic film and non-woven web composite. Since the garment is typically intended for active wear, an exposed backsheet or portions thereof, can be made of materials or of a basis weight which is abrasion resistent.

The backsheet 58 may be constructed of a single spun-bonded polypropylene nonwoven web having a basis weight of about 0.5 oz/yd$^2$ (17 gsm) to about 2.0 oz/yd$^2$ (68 gsm). In the case of a boy's boxer short type article, the cover preferably comprises a material having a basis weight of from about 0.5 oz/yd$^2$ (23.8 gsm) to about 2.0 oz/yd$^2$ (68 gsm). In the case of a girl's skirt type article, the cover preferably comprises a material having a basis weight of from about 0.5 oz/yd$^2$ (23.8 gsm) to about 2.0 oz/yd$^2$ (68 gsm), preferably 1.0 oz./yd$^2$ to 2.0 oz./yd$^2$ at least in the crotch and buttocks regions of the backsheet 58. Lesser basis weights may be used in other regions of the article.

The bodyside liner 56 may be any soft, flexible, porous sheet which passes fluids therethrough. Again, the liner must permit submersion in fresh water, salt water, or treated water and still retain its integrity. The bodyside liner 56 may comprise, for example, a nonwoven web or sheet of a spunbonded, meltblown or bonded-carded web composed of synthetic polymer filaments, such as polypropylene, polyethylene, polyesters or the like, or a web of natural polymer filaments such as rayon or cotton. The bodyside liner 56 has a pore size that readily allows the passage therethrough of liquids, such as urine and other body exudates. The liner 56 may be selectively embossed or perforated with discrete slits or holes extending therethrough. Optionally, the web or sheet may be treated with a surfactant to aid in liquid transfer. One suitable bodyside liner material is a wettable spunbonded polypropylene web produced by the methods and apparatus described in U.S. Pat. No. 4,340,563 issued Jul. 20, 1982, and U.S. Pat. No. 4,405,297 issued Sep. 23, 1983, to Appel et al., which are incorporated herein by reference. Bodyside liner 56 is liquid permeable and is a spunbonded polypropylene nonwoven web having a basis weight of about 0.75 oz/yd$^2$ (25.4 gsm). Suitable adhesives for adhering the laminate layers can be obtained from Findley Adhesives, Inc. of Wauwatosa, Wis.

As described previously, the side panels 26 and 28 may be formed of a material capable of stretching in one direction or capable of stretching in at least two substantially perpendicular directions. One suitable one-directional stretch material is disclosed in U.S. Pat. No. 4,720,415 issued Jan. 19, 1988, to Vander Wielen et al., which is incorporated herein by reference. The one-directional stretch material may comprise a composite material including at least one gatherable web bonded to at least one elongated elastic web. The elastic web may be an elastic film or nonwoven fibrous elastic webs such as meltblown elastomeric fibrous webs. In one embodiment, the side panels 26 and 28 comprise a stretch bonded laminate formed of a prestretched elastic meltblown inner layer sandwiched between and attached to a pair of spunbond polypropylene nonwoven webs having a basis weight of about 0.4 oz/yd$^2$ (13.6 gsm). Suitable elastic materials can be purchased from the Shell Chemical Company of Houston, Tex. under the trade name Kraton. Other suitable one-directional stretch materials are disclosed in U.S. Pat. No. 4,606,964 issued Aug. 19, 1986, to Wideman and U.S. Pat. No. 4,657,802 issued Apr. 14, 1987, to Morman.

The elastic side panel material desirably has stretch characteristic in the first direction such that it is capable of from about 10 to about 500 percent elongation and upon release of tension will recover at least 55 percent of its elongation. It is generally preferred that the side panel material in the first direction be capable of between about 50 and about 300 percent elongation, particularly at least 125 percent elongation and recovery upon release of tension of at least 80 percent of its elongation.

Suitable two-directional stretch materials for the side panels 26 and 28 are disclosed in U.S. Pat. No. 5,114,781 issued May 19, 1992, and U.S. Pat. No. 5,116,662 issued May 26, 1992, to Morman, which are incorporated herein by reference. A two-directional stretch material may comprise a composite material including a neckable material and an elastic sheet, which may be formed by meltblowing or extrusion. Neckable materials are those which may be constricted in at least one dimension by applying a tensioning force in a direction perpendicular to the desired direction of neck-down, and may include a spunbonded, meltblown or bonded carded web. The tensioned, necked neckable material may be joined to the elongated elastic sheet at spaced locations arranged in a nonlinear configuration. Another two-directional stretch composite material may comprise one or more layers of reversibly necked material joined to one or more layers of elastic sheet at spaced locations. Reversibly necked materials are those that have been treated, such as with heat, while necked to impart memory to the material so that, when a force is applied to extend the material to its pre-necked dimensions, the treated, necked portions will generally recover to their necked dimensions upon termination of the force.

The leg and waist elastics 36, 38, 116 and 117 may be formed of a stretch bonded laminate. In particular, the stretch bonded laminate may comprise at least one nonwoven gatherable layer and an elastic layer. Alternately, the leg and waist elastics 36, 38, 116 and 117 may be formed of a dry-spun coalesced multifilament elastomeric thread sold under the tradename LYCRA and available from I. E. Du Pont de Nemours and Company. Still alternately, the elastics 36, 38, 116 and 117 may be formed of other typical elastics utilized in the diaper-making art, such as a thin ribbon of elastic material as disclosed in U.S. Pat. No. 4,940,464 issued Jul. 10, 1990, to Van Gompel et al., which is incorporated herein by reference. Elasticity could also be imparted to the longitudinal side sections by extruding a hot melt elastomeric adhesive between the backsheet 60 and the bodyside liner 62. Other suitable elastic gathering means are disclosed in U.S. Pat. No. 4,938,754 to Mesek and U.S. Pat. No. 4,388,075 to Mesek et al.

The cover 14 can be desirably constructed of a single layer comprising film layer, nonwoven layer, or any other suitable liquid permeable or liquid impermeable material, desirably having a cloth-like feel. The cover 14 is constructed of a single spunbonded polypropylene nonwoven web having a basis weight of about 0.5 oz/yd$^2$ (17 gsm) to about 2.0 oz/yd$^2$ (68 gsm). In the case of a boy's boxer short type article, the cover preferably comprises a material having a basis weight of from about 0.5 oz/yd$^2$ (17 gsm) to about 2.0 oz/yd$^2$ (68 gsm), preferably 1.0 oz./yd$^2$ to 2.0 oz./yd$^2$ at least in the crotch and buttocks regions of the cover 14. In the case of a girl's skirt type article, the cover preferably comprises a material having a basis weight of from about 0.5 oz/yd$^2$ (23.8 gsm) to about 2.0 oz/yd$^2$ (68 gsm). The cover 14 may comprise a second layer of a liquid impermeable film layer suitably joined to the first layer by adhesive. The cover's first layer may be spunbonded polypropylene nonwoven web having a basis weight of from about 0.5 oz/yd$^2$ (23.8 gsm) to about 2.0 oz/yd$^2$ (68 gsm). The cover's second layer may be a polyethylene film ranging from about 0.5 to about 1.0 mil in thickness.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, only one rather than both ends of the waste containment structure can be elastically connected to the cover. Therefore, the invention should not be limited by the specific embodiments described, but only by the claims. The materials of which pant 10 are made can be any materials specifically desired by the user or manufacturer. Numerous examples of materials used in constructing pant 10 and diaper 210 are described in the aforementioned U.S. patents and patent applications incorporated by reference herein.

What is claimed is:

1. An integral disposable waste containment article, comprising:

(a) a waste containment structure, having longitudinal edges and comprising a vapor pervious, liquid pervious backsheet; a soft, flexible porous, fluid-pervious liner, and an absorbent core comprising cellulosic wood fibers and synthetic polymer fibers, wherein the cellulosic wood fibers and synthetic polymer fibers are provided in a cellulosic fiber-to-synthetic polymer fiber ratio between about 30:70 and about 80:20, said absorbent core being contained between the backsheet and the liner;

(b) a set of four elastic-containing side panels, each having edges, a right front side panel and a left front side panel being attached to a front end of the waste containment structure, and a right rear side panel and a left rear side panel being attached to a rear end of the waste containment structure which is opposite the front end of the waste containment structure;

(c) the right front side panel and the right rear side panel being bonded together by ultrasonic sealing, adhesive bonding or heat sealing to form a manually tearable, non-refastenable seam between the right front side panel and the right rear side panel, and the left front side panel and the left rear side panel being bonded together by ultrasonic sealing, adhesive bonding or heat sealing to form a manually tearable, non-refastenable seam between the left front side panel and the left rear side panel, said structure and side panels being configured to have a waist opening, two leg openings, and a crotch area between the leg openings; and (d) a liquid impervious cover, joined to said structure and suspended from the waist opening, the cover being capable of movement relative to the waste containment structure.

2. An integral disposable waste containment article according to claim 1, wherein the cellulosic wood fibers and synthetic polymer fibers are provided in a cellulosic fiber-to-synthetic polymer fiber ratio in the absorbent core between about 60:40 and about 70:30.

3. An integral disposable waste containment article according to claim 1, wherein the absorbent core comprises, in addition, up to five percent of high-absorbency material.

4. An integral disposable waste containment article according to claim 1, wherein the absorbent core comprises, in addition, surfactant to aid in liquid acquisition.

5. An integral disposable waste containment article according to claim 1, comprising in addition leg elastics joined to the backsheet and liner along the edges of the side panels and the longitudinal edges of the waste containment structure in the crotch area of the waste containment structure.

6. An integral disposable waste containment article, comprising:

(a) a waste containment structure, having longitudinal edges and comprising a vapor pervious, liquid pervious backsheet; a soft, flexible porous, fluid-pervious liner; and an absorbent core comprising cellulosic wood fibers and synthetic polymer fibers, wherein the cellulosic wood fibers and synthetic polymer fibers are provided in a cellulosic fiber-to-synthetic polymer fiber ratio between about 30:70 and about 80:20, said absorbent core being contained between the backsheet and the liner;

(b) a set of four ear sections, each having edges, a right front ear section and a left front ear section being attached to a front end of the waste containment structure, and a right rear ear section and a left rear ear section being attached to a rear end of the waste containment structure which is opposite the front end of the waste containment structure;

(c) the right front ear section and right rear ear section being joined together with fasteners, and the left front ear section and the left rear ear section being joined together with fasteners, said structure and ear sections being configured to have a waist opening, two leg openings, and a crotch area between the leg openings; and (d) a front section and a rear section of a liquid impervious cover, joined to said structure and suspended from the waist opening, the cover being capable of movement relative to the waste containment structure; said front section and said rear section of the liquid impervious cover being joined together with fasteners.

7. An integral disposable waste containment article according to claim 6, wherein the cellulosic wood fibers and synthetic polymer fibers are provided in a cellulosic fiber-to-synthetic polymer fiber ratio in the absorbent core between about 60:40 and about 70:30.

8. An integral disposable waste containment article according to claim 6, wherein the absorbent core comprises, in addition, up to five percent of high-absorbency material.

9. An integral disposable waste containment article according to claim 6, wherein the absorbent core comprises, in addition, surfactant to aid in liquid acquisition.

10. An integral disposable waste containment article according to claim 6, comprising in addition leg elastics joined to the backsheet and liner along the edges of the ear sections and the longitudinal edges of the waste containment structure in the crotch area of the waste containment structure.

* * * * *